United States Patent
Totman et al.

(10) Patent No.: US 9,433,459 B2
(45) Date of Patent: Sep. 6, 2016

(54) DEPOSIT ABLATION WITHIN AND EXTERNAL TO CIRCULATORY SYSTEMS

(71) Applicant: ZOLL MEDICAL CORPORATION, Chelmsford, MA (US)

(72) Inventors: Mark Totman, Winchester, MA (US); Sheldon S. White, Brookline, MA (US); Michael R. Dupelle, North Attleboro, MA (US); Christopher Desmarais, Acushnet, MA (US); Paul F. Prew, Attleboro, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 14/039,626

(22) Filed: Sep. 27, 2013

(65) Prior Publication Data
US 2014/0031817 A1      Jan. 30, 2014

Related U.S. Application Data

(63) Continuation-in-part of application No. 13/182,104, filed on Jul. 13, 2011, now abandoned.

(60) Provisional application No. 61/363,876, filed on Jul. 13, 2010, provisional application No. 61/708,426, filed on Oct. 1, 2012.

(51) Int. Cl.
*A61B 18/18* (2006.01)
*A61B 18/14* (2006.01)
(Continued)

(52) U.S. Cl.
CPC ............. *A61B 18/14* (2013.01); *A61N 1/32* (2013.01); *A61B 2018/0041* (2013.01); *A61B 2018/00577* (2013.01); *A61N 1/0408* (2013.01); *A61N 1/20* (2013.01)

(58) Field of Classification Search
CPC .......... A61B 18/14; A61B 2018/0041; A61B 2018/00577; A61N 1/0408; A61N 1/20; A61N 1/32
USPC ................................ 600/372–393; 606/32–45
See application file for complete search history.

(56) References Cited

U.S. PATENT DOCUMENTS 3,834,374 A * 9/1974 Ensanian ................... 600/397
4,706,680 A * 11/1987 Keusch et al. ............. 600/392
(Continued)

FOREIGN PATENT DOCUMENTS

| CN | 1631327 A | 6/2005 |
| EP | 0 252 732 A2 | 1/1988 |

(Continued)

OTHER PUBLICATIONS

Notification of Transmittal of the International Search Report and Written Opinion of the International Searching Authority from corresponding PCT/US2013/062257 dated Jan. 3, 2014.
Alexandrov et al., Ultrasound Enhanced Thrombolysis in Acute Arterial Ischennia, Ultrasonics vol. 48, #4 Aug. 2008.
(Continued)

*Primary Examiner* — Michael Peffley
*Assistant Examiner* — Amanda Zink
(74) *Attorney, Agent, or Firm* — Fish & Richardson P.C.

(57) ABSTRACT

Systems and methods of electrical stimulation for intra and extra vascular treatment of a subject are provided. The device includes a first electrode, a second electrode, and a controller. The controller is configured to apply an electrical current between the first and second electrodes. The electrical current follows a path between the first and second electrodes and through a portion of the subject that includes a blockage.

4 Claims, 7 Drawing Sheets

(51) Int. Cl.
*A61N 1/32* (2006.01)
*A61N 1/04* (2006.01)
*A61N 1/20* (2006.01)
*A61B 18/00* (2006.01)

(56) References Cited

U.S. PATENT DOCUMENTS

| | | | |
|---|---|---|---|
| 5,540,722 A * | 7/1996 | Clare | A61B 18/12 600/522 |
| 5,569,245 A | 10/1996 | Guglielmi et al. | |
| 5,622,168 A * | 4/1997 | Keusch et al. | 600/391 |
| 5,725,563 A | 3/1998 | Klotz | |
| 5,952,398 A | 9/1999 | Dietz et al. | |
| 6,210,404 B1 | 4/2001 | Shadduck | |
| 6,360,123 B1 | 3/2002 | Kimchi et al. | |
| 7,092,753 B2 | 8/2006 | Darvish et al. | |
| 7,842,076 B2 | 11/2010 | Zikorus et al. | |
| 8,046,061 B2 | 10/2011 | Chen et al. | |
| 8,827,992 B2 * | 9/2014 | Koss et al. | 606/33 |
| 2004/0039417 A1 * | 2/2004 | Soykan et al. | 607/2 |
| 2006/0089638 A1 | 4/2006 | Carmel et al. | |
| 2006/0142824 A1 | 6/2006 | Zikorus et al. | |
| 2007/0118177 A1 | 5/2007 | Libbus et al. | |
| 2007/0129718 A1 | 6/2007 | Donovan | |
| 2008/0195174 A1 | 8/2008 | Walker et al. | |
| 2009/0247933 A1 | 10/2009 | Maor et al. | |
| 2010/0004623 A1 | 1/2010 | Hamilton, Jr. et al. | |
| 2010/0121317 A1 | 5/2010 | Lorang et al. | |
| 2011/0190659 A1 | 8/2011 | Long et al. | |
| 2012/0016361 A1 | 1/2012 | White et al. | |
| 2014/0039579 A1 * | 2/2014 | Mashiach et al. | 607/61 |

FOREIGN PATENT DOCUMENTS

| | | |
|---|---|---|
| EP | 2127694 A1 | 12/2009 |
| WO | 03089054 A2 | 10/2003 |
| WO | 2009094554 A2 | 7/2009 |

OTHER PUBLICATIONS

Ana Huttenlocher, et al., Wound Healing With Electric Potential, Clinical Implications of Basic Research, The New England Journal of Medicine, Jan. 18, 2007, pp. 303-304.

Extended European Search Report from related European Application No. 11807460.8 dated Nov. 18, 2013.

International Search Report and Written Opinion from related International Application No. PCT/US2011/043871, dated Nov. 9, 2011.

Johannes Gorich, et al., Mechanical Thrombolysis of Acute Occulsion of Both the Superficial and HTE Deep Femoral Arteries Using a Thrombectomy Device, May 1998, pp. 1177-1180.

Katoh et. al., Noninvasive Extracorporeal Thrombolysis Using Electrical Discharge-Induced Shock Waves: In Vitro Experiments Investigative Radiology vol. 39, #4, 2004.

Muller-Hulsbeck et al., Mechanical Thrombolysis Devices, Cardiovascular and Interventional Radiology, vol. 27.

N. Rilinger, et al., Mechanical Thrombectomy of Embolic Occlusion in Both the Profunda Femoris and Superficial Femoral Arteries in Critical Limb Ischaemia, The British Journal of Radiology, 70 (1997), 80-84.

S. Atar, Perspectives on the Role of Ultrasonic Devices in Thrombolysis, Journal of Thrombosis and Thrombolysis, 17(2), 107-114, 2004.

The 21st Scientific Meeting of the International Society of Hypertension, 5th Asian-Pacific Congress of Hypertension, Global Challenge for Overcoming High Blood Pressure, 2 pages, ISH 2006, Oct. 15-19, 2006 Fukuoka, Japan.

Valeri S. Chekanov, et al., Slowed Progression or Elimination of Atherosclerosis by Low-Frequency Electrical Impulses, Milwaukee Heart Institute, Heart Care Associates at Sinai Samaritan Medical Center, St. Luke's Medical Center, Milwaukee, Wisconsin, 2003; 18:47-58.

Valeri S. Chekanov, Low Frequency Electrical Impulses Reduce Atherosclerosis in Cholesterol FED Rabbits, Med Sci Monit, 2003; 9(8): BR302-309.

* cited by examiner

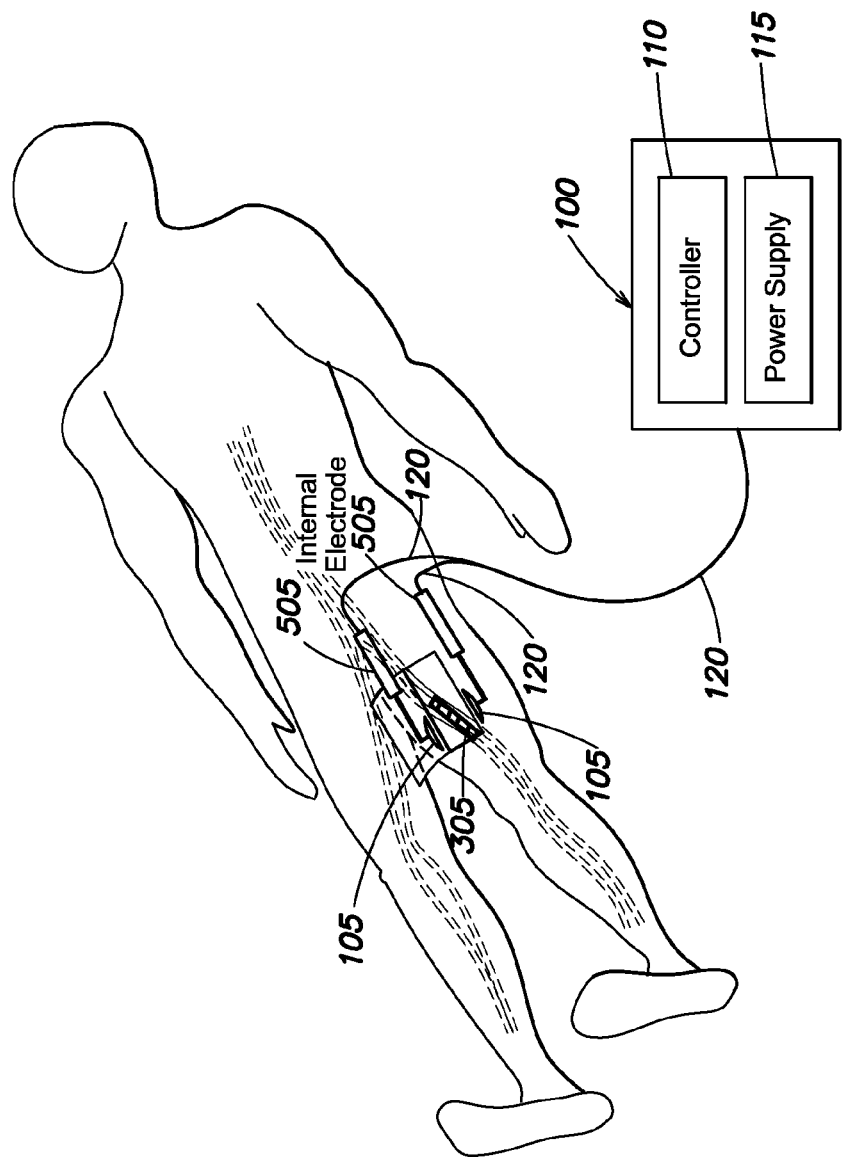
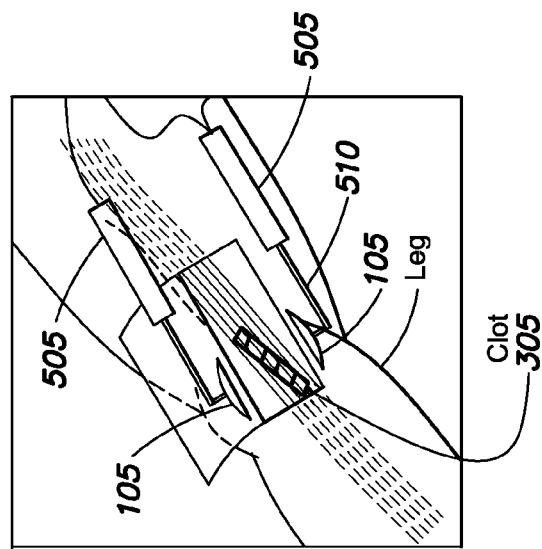
FIG. 7
FIG. 8

DEPOSIT ABLATION WITHIN AND EXTERNAL TO CIRCULATORY SYSTEMS

CROSS REFERENCE TO RELATED APPLICATIONS

This application claims priority under 35 U.S.C. §119(e) to U.S. Provisional Application Ser. No. 61/708,426 titled "Deposit Ablation Within and External to Circulatory Systems", filed Oct. 1, 2012, which is incorporated herein by reference in its entirety. This application also claims priority under 35 U.S.C. §120 to U.S. patent application Ser. No. 13/182,104 titled "Deposit Ablation Within and External to Circulatory Systems", filed Jul. 13, 2011, now abandoned, which claims priority under 35 U.S.C. §119(e) to U.S. Provisional Application Ser. No. 61/363,876 titled "Deposit Ablation Within and External to Circulatory Systems", filed Jul. 13, 2010, each of which is incorporated herein by reference in its entirety.

BACKGROUND OF THE INVENTION

1. Field of Invention

At least one embodiment of the present invention relates generally to vascular circulation, and more specifically, to systems and methods that can enhance vascular circulation or improve health by reducing or eliminating thrombi, clots, or plaque in a subject's circulatory system, or external to the subject's circulatory system, such as in an organ or duct.

2. Background

Thrombi, blood clots, plaque buildup, and other obstructions within blood vessels of the circulatory system pose a health risk to the general population. These conditions can occur due, for example, to genetic conditions, eating habits, exercise or lack thereof, and other lifestyle choices. Various efforts to mitigate circulatory system ailments are intrusive, costly, have limited success rates, or may have side effects and recovery times that can also negatively impact a patient's health. Vascular obstructions continue to claim lives and reduce the quality of life of numerous people throughout the world.

SUMMARY

Aspects and embodiments are directed to systems and methods of vascular treatment of a subject. An electrical current can be applied to blockages in a subject's blood vessel. This causes the blockages to ablate, fragment, dissolve, or decrease in size or volume. This reduces impedance to blood flow through the circulatory system.

At least one aspect is directed to an electrical stimulation device for vascular treatment of a subject. The device includes a first electrode, a second electrode, a controller, and a power source. The controller and power source are configured to apply an electrical current between the first and second electrodes in pulses and at a frequency adapted to ablate a blockage in a blood vessel of the subject. The electrical current follows a path between the first and second electrodes and through a portion of the blood vessel that includes a blockage.

At least one other aspect is directed to a method of ablating a blockage in a circulatory system of a subject. The method positions a first electrode and a second electrode proximate to the blockage in a blood vessel of the subject. The method also controls an electrical current pulses having a frequency suitable to ablate the blockage. The current follows a path between the first electrode and the second electrode, and through the blockage.

At least one other aspect is directed to a method of facilitating vascular care of a subject. The method provides an electrical stimulation device including a first electrode, a second electrode, a controller, and a power source. The electrical stimulation device is configured to apply pulses of an electrical current between the first electrode and the second electrode at a frequency adapted to ablate a blockage location in a portion of the blood vessel of the subject. The electrical current follows a path between the first electrode, the portion of a blood vessel that includes the blockage, and the second electrode.

At least one other aspect is directed to an electrical stimulation device for treatment of a subject. The device includes a first electrode and a second electrode. The device also includes a controller and a power source configured to apply an electrical current in pulses and at a frequency adapted to ablate a blockage between the first electrode and the second electrode in the subject. Electrical energy follows a path between the first electrode, the blockage, and the second electrode.

In various embodiments, the first and second electrodes are external electrodes. In some embodiments, the first and second electrodes are internal electrodes. The first and second electrodes can be positioned internal to the subject, proximate to an outer surface of the blood vessel of the subject, and external to the blood vessel. The first and second electrodes can also be positioned internal to the subject, proximate to substantially opposite portions of an outer surface of the blood vessel, and proximate to the blockage. A location of the blockage in the blood vessel can be identified.

In some embodiments, the electrical stimulation device includes a fiber optic device to guide the first electrode to a first position internal to the subject and proximate to a first portion of an outer surface of the blood vessel, and to guide the second electrode to a second position internal to the subject and proximate to a second portion of the outer surface of the blood vessel. The first portion of the outer surface and the second portion of the outer surface can be located proximate to the blockage.

In various embodiments, the first and second electrodes apply the electrical current to the blockage. The electrical current can have a value of between 20 mA and 80 mA, and the device can apply a voltage of substantially 20 volts across the portion of the blood vessel that includes the blockage. These current and voltage levels can be adjusted based on the size of the subject and the subject's tolerance or comfort level when exposed to electrical current. In one embodiment, the current is applied at a frequency of 50-100 pulses per minute. In another embodiment, the electrical current has a value of approximately 15 mA, a pulse duration between approximately 80 and 175 milliseconds, and the electrical pulses are applied at a frequency between about 100 and 175 pulses per minute for a duration of approximately 30 to 75 minutes. In yet another embodiment, the electrical current has a value of between approximately 2 and 8 mA, a pulse duration of approximately 2 milliseconds, and the electrical pulses are applied at a frequency between about 50 and 100 pulses per minute for a duration of approximately one to eight hours. In some embodiments, the device includes at least one of an external defibrillator and a pacing unit.

In some embodiments, electrical current is applied to the blockage and the blockage fragments. The first and second electrodes can be removed from the subject after the electrical current has been applied to the subject. The electrical current can be applied to the blockage with the first electrode positioned internal to the subject, external to the blood vessel that includes the blockage, and proximate to a first portion of an outer surface of the blood vessel. The electrical current can be applied to the blockage with the second electrode positioned internal to the subject, external to the blood vessel that includes the blockage, and proximate to a second portion of the outer surface of the blood vessel.

In some embodiments, the first electrode is positioned external to the subject, proximate to the blockage, the second electrode is positioned external to the subject, proximate to the blockage, and the electrical current is applied to the blockage. In one embodiment, the blockage includes plaque or a thrombus, and the electrical current dissolves the plaque or thrombus. In one embodiment, the controller is configured to ablate a blockage such as a deposit located external to a circulatory system of the subject. For example, the deposit can be located in a duct or an organ of the subject.

In various embodiments, instructions to operate the electrical stimulation device are provided. The instructions can include at least one instruction directing a user to identify a location of the portion of the blood vessel that includes the blockage. The instructions can also direct the user to position a first electrode and a second electrode proximate to the location of the portion of the blood vessel that includes the blockage, and to control an electrical current to follow a path between the first electrode and the second electrode that includes the blockage. In some embodiments, the instructions can direct the user to position the first electrode internal to the subject, external to the blood vessel that includes the blockage, and proximate to a first portion of an outer surface of the blood vessel, and to position the second electrode internal to the subject, external to the blood vessel that includes the blockage, and proximate to a second portion of the outer surface of the blood vessel. The instructions can also instruct the user to apply the electrical current to the blockage.

In some embodiments, the instructions can direct the user to position the first electrode external to the subject, proximate to the blockage, to position the second electrode external to the subject, proximate to the blockage, and to apply the electrical current to the blockage. The instructions can also direct the user to apply the electrical current to the blockage, and to remove the first electrode and the second electrode from the subject subsequent to application of the electrical current.

Other aspects and embodiments are discussed below. Both the foregoing information and the following detailed description are illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain the described and claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 7 is a perspective view depicting an electrical stimulation device with internal electrodes in accordance with an embodiment;

FIG. 8 is a perspective view depicting an electrical stimulation device with internal electrodes in accordance with an embodiment;

DETAILED DESCRIPTION

Figure 1:
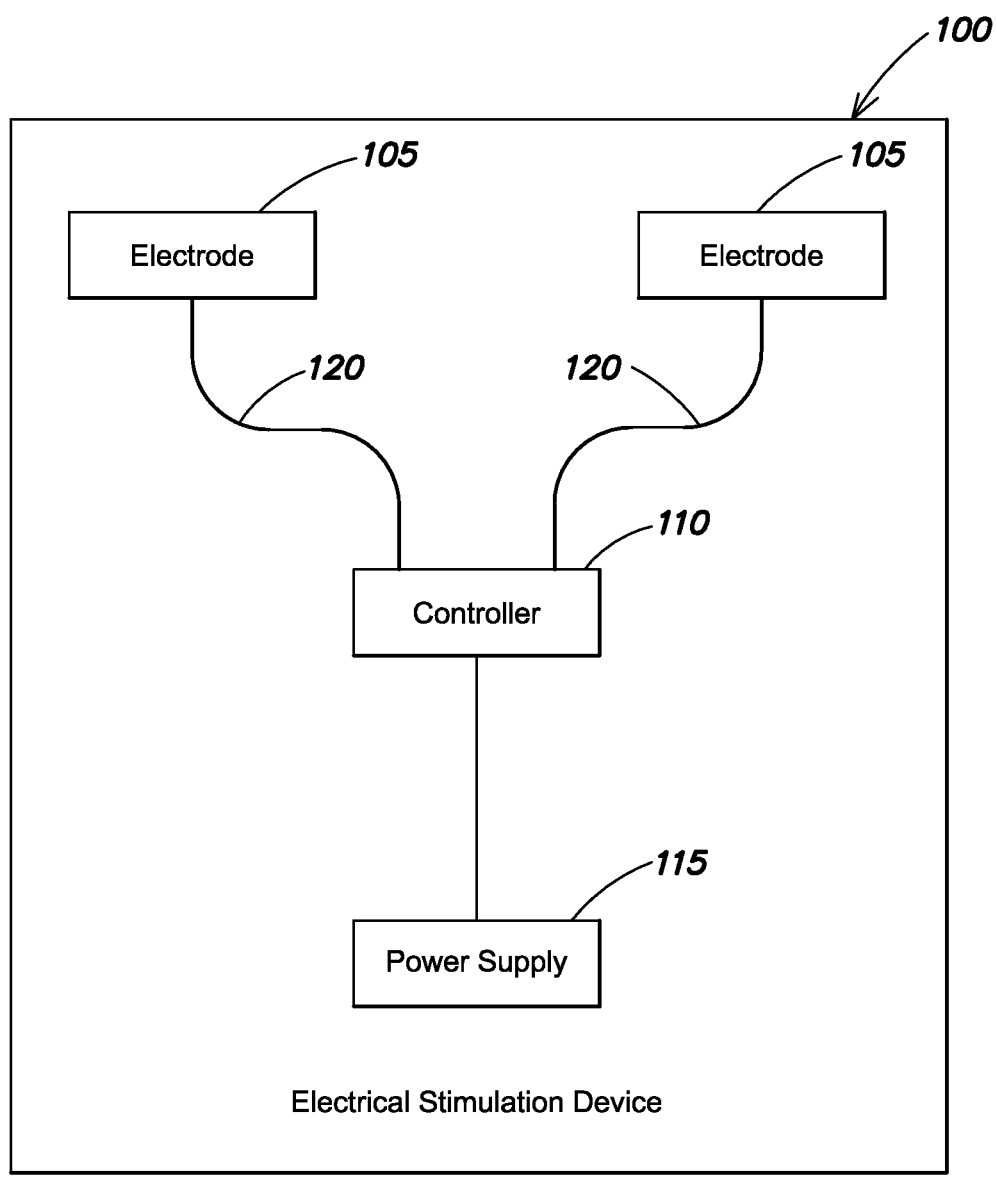
FIG. 1 is a block diagram depicting an electrical stimulation device for vascular treatment of a subject in accordance with an embodiment.

The systems and methods described herein are not limited in their application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter, equivalents thereof, and additional items, as well as alternate embodiments consisting of the items listed thereafter exclusively.

Various aspects and embodiments are directed to vascular treatment of a subject. Although embodiments are described with respect to a human subject, the aspects and embodiments described herein may be used with other subjects, such as animals. At least one electrode is placed proximate to a subject and electrical current is applied to the subject. The electrical current passes through a blockage in a blood vessel of the subject, and electrical energy from the applied current ablates the blockage, facilitating circulatory system blood flow.

FIG. 1 illustrates a block diagram depicting electrical stimulation device 100 for vascular treatment of a subject. In one embodiment, electrical stimulation device 100 includes at least one electrode 105, at least one controller 110, and at least one power supply 115. Controller 110 and power supply 115 can be electrically connected to electrodes 105 by at least one wire 120, which may be shielded or insulated. Electrodes 105 may be part of device 100, or separate elements that are coupled to device 100 by wires 120.

In one embodiment, electrodes 105 are placed proximate to a subject. For example, electrodes 105 can be external electrodes configured for placement on the skin of a subject. Conductive materials such as gels can permeate non-conductive materials such as clothes, which can be present between electrodes 105 and the subject's skin, in order to create an electrical connection or closed circuit between at least two electrodes 105. In one embodiment, electrodes 105 are placed on a subject proximate to a blockage in a blood vessel of the subject. For example, a blockage may be identified in a blood vessel of one of the subject's limbs, such as a leg. In this example at least one electrode 105 can be an external electrode placed on the subject's leg at a point generally nearest to the blockage. Electrode 105 can also be an internal electrode placed inside the subject, for example proximate to an outer surface of the blood vessel that includes the blockage. The internal electrode can be placed inside the subject during a surgical procedure, and may be guided into position by a fiber optic device. After treatment, the internal electrode may be removed. In one embodiment, a plurality of electrodes 105 are in a matrix or vector configuration about the subject, either externally or internally, and this array of electrodes 105 is configured to collectively focus electrical energy through the blockage. For example, a multiplicity of electrodes 105 may be arranged to create power vectors. The power vectors can be arranged in a pattern that concentrates their applied energy on specific locations of the subject, e.g., the location including the blockage, rather than a more diffuse application that may occur when there are exactly two electrodes 105.

In one embodiment, two electrodes 105 are placed on the subject, internally or externally, proximate to the blockage. Controller 110 directs power supply 115 to provide electrical current to at least one of the two electrodes 105. The current can be applied to the subject via electrodes 105 as a series of pulses, for example, as a square wave. The current follows a path between the two electrodes 105. In one embodiment, the amount of energy delivered to a human subject to ablate the blockage is approximately equal to the amount of energy, in joules, delivered to a human subject during approximately 8 hours of a cardiac pacing procedure. The blockage can include at least one of a thrombus, a clot in a blood vessel, plaque, fibrin, fatty deposits, collections of any of red blood cells, white, blood cells, platelets, or other matter than can obstruct blood flow, and combinations thereof. The blockage can be in a fixed position in a blood vessel. The blockage may include a total blockage or a partial blockage that restricts blood flow but does not eliminate it entirely.

In one embodiment, controller 110 and power supply 115 are part of electrical stimulation device 100, with power supply 115 providing electrical power to electrodes 105. Other configurations are possible. For example, controller 110 and power supply 115 can be separate from electrical stimulation device 100. In some embodiments, electrodes 105 and power supply 115 have separate controllers 110 and controller 110 can be powered by separate or additional power sources. In one embodiment, power supply 115 powers electrical stimulation device 100, and device 100 includes another medical device, such as an external cardiopulmonary resuscitation device, a transcutaneous electrical nerve stimulation (TENS) unit, a transcutaneous external pacing unit, or an automatic external defibrillator unit. In one embodiment, electrical stimulation device 100 is part of a universal external defibrillator or pacing device such as the M Series®, R Series®, or E Series® defibrillator devices manufactured by the ZOLL® Medical Corporation of Chelmsford Mass. Power supply 115 may include batteries or other power supplies, including AC power supplies and uninterruptable power supplies.

In one embodiment, electrical stimulation device 100 includes dedicated control logic devices that collectively constitute controller 110. Such dedicated control logic can include programmable logic devices and arrays, application specific integrated circuits, hardware and software combinations, general purpose processors and dedicated controllers, for example. Further, electrical stimulation device 100 may include graphical user interfaces or other interfaces to provide output information and receive input information from a user.

In one embodiment, electrodes 105 ablate, fragment, or dissolve a blockage in the blood vessel by providing current along a path between two electrodes 105 that are positioned proximate to the portion of the blood vessel that includes the blockage. Electrodes 105 can be configured to be positioned in, on, or about the subject so that current follows a path between them and through a blockage. Electrodes 105 may be positioned externally (e.g., on or near the patient's skin and near the portion of the blood vessel that includes the blockage) or internally (e.g., on or near an outside surface of the portion of the blood vessel that includes the blockage).

In one embodiment, the electrical current between two electrodes 105 and through the blockage in the blood vessel ablates the blockage in the absence of stents, vascular surgery, ultrasound, mechanical removal, and drugs. For example, the location of the blockage or physical condition of the subject may make vascular surgery or drugs undesirable. The electrical current between two electrodes 105 can also complement drugs or other treatment to ablate blockages or other deposits in the subject. The electrical current could be used in this embodiment specifically in concert with drug or other procedural therapy.

In one embodiment, controller 110 controls the application of current to the blockage that is electrically coupled between two electrodes 105. For example, in one illustrative embodiment in which current was applied to a mouse weighing approximately 50 g, a pulsed current of approximately 5 mA with an applied voltage of 2.5V to 5V was applied in pulses to the body of a mouse with no ill effects on the mouse. The pulses of current had a duration of approximately 40 ms and were applied to the body of the mouse at a frequency of approximately 100 pulses per minute for a period of approximately 45 minutes. Two electrodes 105 having a treatment area of 0.2 square inches per electrode were placed transthoracic on the body of the mouse. The electrodes 105 were formed from a tin conductor and used a 10% potassium chloride conductive gel, available from Parker Laboratories, Inc. of Fairfield N.J., with a combined impedance of approximately 750 Ohms. The amount of energy applied to the body of the mouse over this period of time was approximately 30 Joules/lb. It should be appreciated that a higher frequency of shorter pulses could alternatively be used. For example, in one clinical test, it was empirically determined that shorter pulses applied to the body of a mouse at a frequency of between about 1000 pulses per minute and about 3000 pulse per minute minimized the level of pain exhibited by the mouse.

For use on a human subject, a similar amount of energy per unit weight (e.g., 30 Joules/lb) could be applied to the human subject using a pulsed direct current having a value between 20-80 mA and an associated voltage potential of less than approximately 20V. For example, an 80 mA current may be applied in pulses having a duration of 40 ms at a frequency of 100 pulses per minute for 8.7 hours. This amount of energy applied to the body of a human subject weighing 175 lbs and having an impedance of approximately 400 Ohms (i.e., the combined impedance of the circuit including the electrodes, any conductive gel on the surface of the electrodes, and the impedance of that portion of the subject's body disposed between the electrodes 105) corresponds to approximately 30 Joules/lb, and is equivalent to the amount of energy that would be applied to the human subject during 8.7 hours of pacing. It should be appreciated that dependent on the size, weight, and health of the subject, the subject's sensitivity to the applied energy, whether the subject was conscious or not during the procedure, etc. these values of current, voltage, and time may vary. In general, for a human subject that is conscious during the procedure, the pulsed electrical current may be applied using external electrodes with a value of 20-80 mA, a duration of approximately 30-50 ms, an associated voltage potential of less than approximately 20V, and at a frequency between about 50-100 pulses per minute for a duration of between 7-10 hours. Other values and ranges, less than 20 mA, greater than 80 mA, and more or less than 20V are possible. Where the electrodes 105 are disposed internally, lesser amounts of energy may be required. For example, where internal electrodes are used, current values may be below 20 mA. It should be appreciated that aspects of the present invention are not limited to the application of current in pulses, as a direct current may provide similar benefits. For example, to provide a similar amount of energy to the body of the human subject might require providing 10 mA of current to the body of the subject for 24 hours.

In one clinical experiment, pulses of current were applied to human subject in pulses having a duration of 2 ms at a frequency between about 50-100 pulses per minute. In this experiment, the pulses of current had an amplitude between 2-8 mA and an associated voltage potential of less than approximately 20V, and the subject experienced little or no discomfort. Such pulses of current could thus be applied to the body of a human subject for a duration of 1-8 hours to ablate a thrombus, with little or no discomfort while the subject was conscious.

Blockages such as clots, plaque, or thrombi are reduced in size by the electrical current. In one embodiment, the current induced ablation process may be enhanced by surface features of the blockage. For example, electrical current concentration on boundaries or cracks of the blockage can aid in its ablation. The resulting blockage fragments are sufficiently small to avoid blocking blood vessels and travel through the circulatory system. For example, blockage fragments can be sub-cellular, smaller than the inner diameter of capillaries, or smaller than red blood cells to reduce the risk of downstream blockage.

In one embodiment, controller 110 can use electrodes 105 to determine the impedance of the subject proximate the blockage. The impedance determination or measurement can be made prior to, during, after, or between treatment and includes impedance attributable to electrodes 105, any conductive fluid on the surfaces of electrodes 105, as well as the impedance of the subject's body between electrodes 105. For example, the impedance of the subject proximate the blockage may be measured prior to treatment and used to adjust the voltage or current to be delivered to the subject. For example, where the impedance of the subject proximate the blockage is high (e.g., 400 Ohms) a lower value of current may be used, and where the impedance of the subject proximate the blockage is low (e.g., 25 Ohms) a higher value of current may be used. During treatment, as the blockage ablates, the impedance may drop, indicating at least partial success in the ablation therapy. Controller 110 can identify the decrease in impedance, and reduce the frequency or amplitude of the current delivered via electrodes 105. In one embodiment, controller 110 increases the current when impedance measurements indicate that the clot or blockage is not responding to an earlier application of treatment. The current that is applied to the blockage may be applied in a single direction (i.e. with a first electrode 105 acting as a cathode and a second electrode 105 acting as an anode), or in different directions at different times (i.e., with a first electrode acting as the cathode during a first time period and acting as the anode during a second time period). In one embodiment, controller 110 can reverse the polarity of the electrical current applied via the electrodes 105. In an alternative embodiment, the electrodes 105 may be physically moved to swap position on the subject to reverse the direction of current flow.

In one embodiment, electrodes 105 are located in a housing constructed to be placed about a limb or other body part (e.g., thorax or abdomen) of the subject. The housing may include one, two, or more than two electrodes 105. The housing can have the shape of a sleeve configured for placement around a limb, and can be made of a flexible material, such as nylon or other polymers, as well as cotton, cloth, rubber, or other synthetic or non-synthetic materials. The housing may also have a generally fixed, rigid shape that includes hard plastic material. In one embodiment, the housing can include at least one electrode 105 and completely wraps around a portion of a limb and is secured in this configuration by hook and loop fasteners, adhesives, buttons, clips, zippers, strings that are tied together, elastics, ribs, reinforced bands, and other fasteners. In one embodiment, electrodes 105 are integral to the housing and affixed in a generally permanent manner. For example, electrodes 105 can be sewn into an inner surface of the housing, facing the subject, when the housing is a nylon sleeve, or affixed to an inner surface of the housing when the housing is a rigid plastic case. In another embodiment, electrodes 105 are not disposed in any housing and are free standing electrodes that are in electrical contact with the subject's body. Electrodes 105, with or without a separate housing element, wrap around a portion of the subject, such as the subject's skin for external electrodes 105, or a blood vessel of the subject for internal electrodes 105. In one embodiment, an adhesive fixes electrodes 105 (internal or external) to a portion of the subject.

Figure 2A:
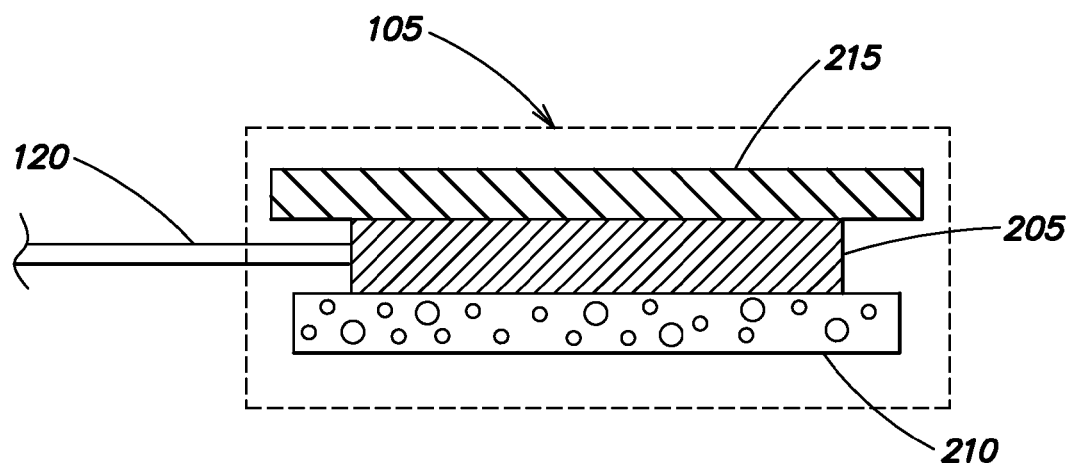
FIG. 2A is a perspective view depicting an electrical stimulation device electrode configured for external placement proximate to a subject in accordance with an embodiment.
Figure 2B:
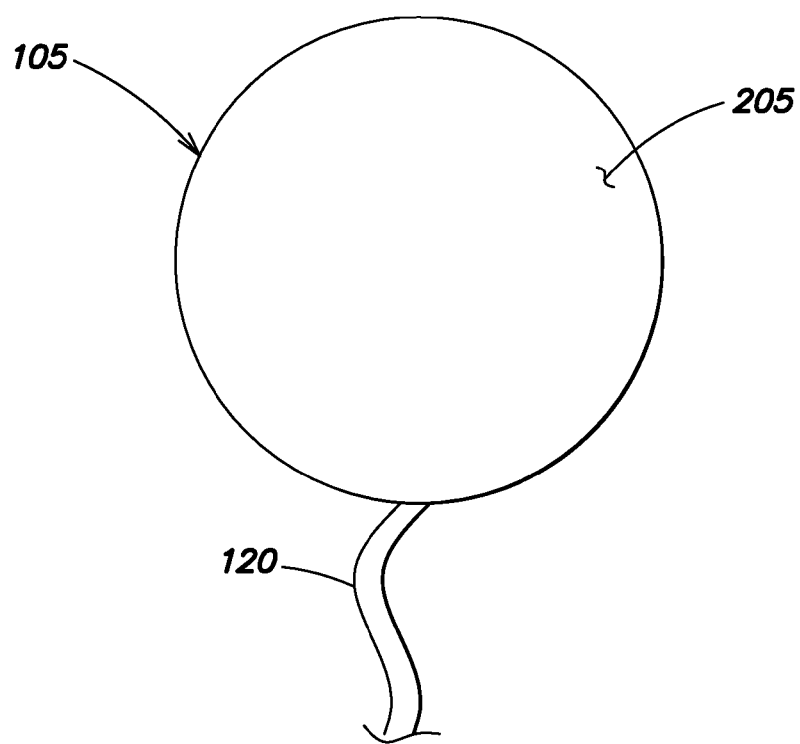
FIG. 2B is a plan view depicting an electrical stimulation device electrode configured for external placement proximate to a subject in accordance with an embodiment.

FIG. 2A and FIG. 2B illustrate electrodes 105 in accordance with one embodiment of the present invention. In this embodiment, electrode 105 includes a pair of electrodes for placement on the subject near a blood vessel blockage. In this example, the pair of electrodes 105, a portion of the blood vessel and the blockage form at least part of a circuit so that current follows a path between the pair of electrodes 105 and through the blockage, causing blockage ablation. Other configurations are possible, such as an array of electrodes 105 configured to form at least one electrical circuit that includes at least a portion of a blockage in a blood vessel between at least two electrodes 105. In one embodiment, different pairs of electrodes 105 provide current to different blockages or different portions of the same blockage, either simultaneously or sequentially.

With reference to FIGS. 2A and 2B, in one embodiment electrode 105 is configured for external contact with the patient, (e.g., the patient's skin) and includes at least one electrically conductive plate 205. Conductive plate 205 can be exposed to contact the subject when placed in or on part of the subject's body. Electrodes 105 can contact the subject directly, e.g., via contact between the subject and conductive plates 205; or indirectly, e.g., with intervening elements to facilitate conductivity, or intervening elements such as the subject's clothes, part of a housing, or a protective material inserted between the subject's skin and electrode 105. For example, conductive fluid 210 such as a conductive gel, a conductive adhesive, or a conductive solid such as a paste can be applied to conductive plate 205, or to the subject's body at the location where conductive plate 205 is brought into contact with the subject. In one embodiment, conductive fluid 210 includes a conductive hydrogel that is applied to a surface of conductive plate 205 to cover at least part of that surface, which directly or indirectly contacts the subject's skin.

In one embodiment, insulating layer 215 is affixed with, for example, an adhesive, to a surface of electrode 105 that does not make an electrical connection with the subject. This prevents unwanted electrical connections with the user of the electrical stimulation device or with parts of the subject's body other than the portion of the blood vessel that includes the blockage.

Figure 4:
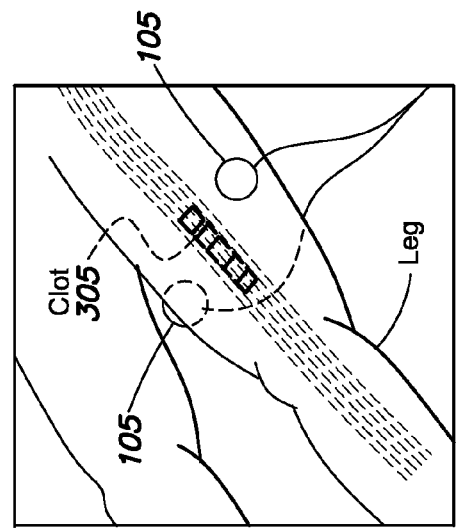
FIG. 4 is a perspective view depicting an electrical stimulation device with external electrodes in accordance with an embodiment.
Figure 3:
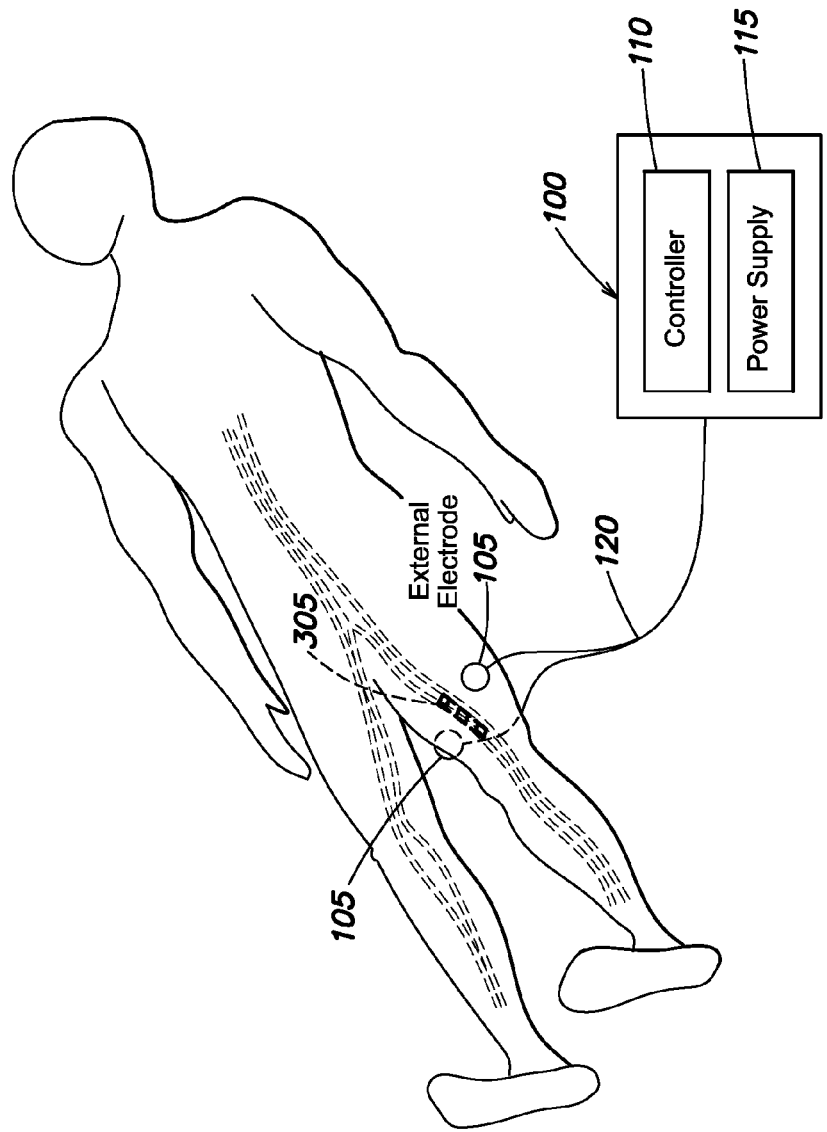
FIG. 3 is a perspective view depicting an electrical stimulation device with external electrodes in accordance with an embodiment.

FIG. 3 and FIG. 4 illustrate device 100 with external electrodes 105. In the illustrative embodiment of FIGS. 3 and 4, blockage 305 has been identified in a blood vessel of one of the subject's legs. Blockage 305 may also be located in blood vessels of other areas of the subject's body, such as other limbs, arms, legs, hands, feet, shoulders, neck, thorax or abdomen. Alternatively, blockage 305 may be a deposit located outside blood vessels, and may include calcium, crystallized mineral, plaque, lesions, scleroses, or other solid deposits in ducts, the heart, or other organs such as the gall bladder. Blockage 305 may also include deposits in the gall bladder, kidney, or bladder stones, as well as deposits throughout the subject's body associated with Alzheimer's disease, arthritis, or multiple sclerosis. In one embodiment, two electrodes 105 are positioned proximate to an identified blockage 305. For example, electrodes 105 can be external electrodes configured to be positioned on the subject's skin in the portion of the subject's body proximate to blockage 305.

With reference to FIGS. 3 and 4, electrodes 105 can be external electrodes positioned about the subject's leg, proximate to blockage 305 and coupled to device 100 by wires 120. In some embodiments, device 100 includes a defibrillator or pacing machine, as well as controller 110 and power supply 115. Power supply 115 may include a battery or AC power source, such as a connection to main lines in an outlet. In one embodiment, with electrodes 105 positioned proximate to blockage 305, device 100 provides electrical current between two electrodes 105 and blockage 305. This current may be pulsed, cyclical, repetitive, or continuous. The user (e.g., a doctor) can initiate application of the electrical current by inputting instructions to device 100 via a user interface. The electrical current follows a path between, for example, two electrodes 105 and through blockage 305 and other parts of the subject's body, such as the areas of skin that are in electrical contact with at least one electrode 105. Subsequent to treatment, the device operator may remove electrodes 105 and examine the subject to determine the extent to which blockage 305 has ablated.

Figure 5:
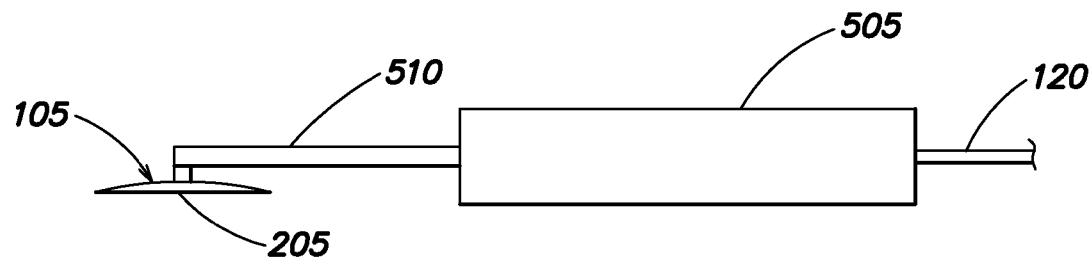
FIG. 5 is a perspective view depicting an electrical stimulation device electrode configured for internal placement proximate to a blood vessel of a subject in accordance with an embodiment.
Figure 6:
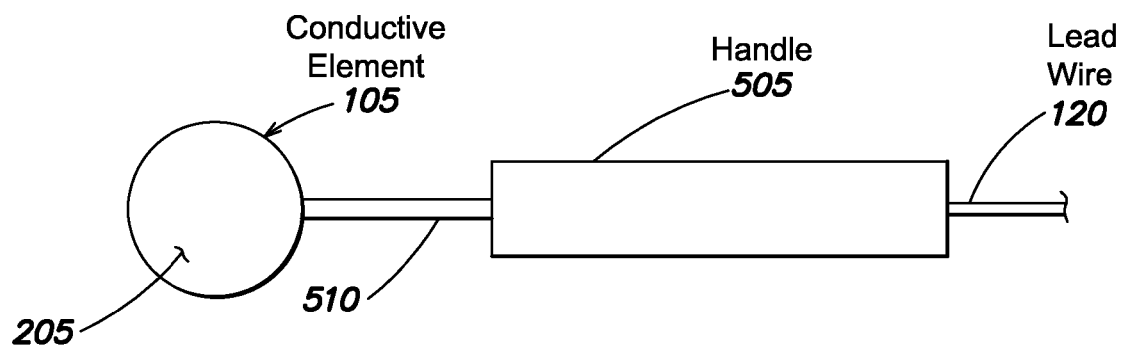
FIG. 6 is a plan view depicting an electrical stimulation device electrode configured for internal placement proximate to a blood vessel of a subject in accordance with an embodiment.

FIG. 5 and FIG. 6 illustrate electrodes 105 configured for placement internal to the subject. For example, two electrodes 105 may be positioned internal to the subject and proximate to an outer surface of the blood vessel that contains blockage 305 so that current may follow a path between the two electrodes 105 and blockage 305. In this example, electrodes 105 remain external to the blood vessel. Handle 505 and extending member 510 couple electrode 105 with insulated wire 120. Extending member 510 can be substantially rigid and include or couple to wire 120. In one embodiment, extending member 510 is the insulated wire 120 itself, and has substantially the same flexibility as the rest of the length of wire 120. A user, such as a doctor, grips handle 505 and guides electrode 105 through an incision that has been made in the subject in the general vicinity of the identified blockage. In this example, the user can position the conductive plates 205 of respective electrodes 105 sufficiently close to the blockage so that current from power supply 115 can pass through the blockage via the two electrodes 105. In one embodiment, the user positions two electrodes 105 about the portion of the blood vessel that includes the blockage. Fiber optics or surgical incisions into the patient can assist in guiding electrodes 105 to their desired position on, for example, opposite sides of the outer surface of the blood vessel proximate to blockage 305. This may be done substantially simultaneously or in a subsequent manner, where the user positions one electrode 105 with one hand and one electrode 105 with the other hand. For example, two electrodes 105 can be positioned proximate to different portions of the outer surface of the blood vessel, about the blockage, so that the current follows a path between the two electrodes and through the blockage. In one embodiment, the user holds electrodes 105 in place during application of electric current to blockage 305, or electrodes 105 can be otherwise fixed in their position, for example by wrapping electrodes 105 around a portion of the subject, or by adhering electrodes 105 to a portion of the subject (e.g., an external surface of a blood vessel) with an adhesive.

FIG. 7 and FIG. 8 illustrate device 100 with internal electrodes 105. In the illustrative embodiment of FIGS. 7 and 8, blockage 305 has been identified in a blood vessel of one of the subject's legs. Blockage 305 may also be located in blood vessels of other areas of the subject's body as noted previously. The user of device 100 can position two electrodes 105 internal to the subject and proximate to an outer surface of the blood vessel that includes an identified blockage 305. This positioning of electrodes 105, proximate to an outer surface of the blood vessel that includes blockage 305, includes positioning electrodes 105 adjacent to and touching the outer surface of the blood vessel, as well as positioning electrodes 105 near the outer surface the blood vessel without making direct contact. For example, electrodes 105 may be positioned to contact tissue or muscles between conductive plate 205 of electrode 105 and the outer surface of the blood vessel. This proximate positioning includes locating electrodes 105 in an area sufficient to allow current to pass between at least two electrodes 105 and blockage 305. The pulsed, cyclical, repetitive, or continuous current may also pass through additional tissue, muscle, or organic matter, including the walls of the blood vessel that include blockage 305.

The user may also perform the minimally invasive surgical procedure in the vicinity of blockage 305 to allow for the internal positioning of electrodes 105. In one embodiment, internal electrodes 105 are positioned internal to the subject and outside the blood vessel. Electrodes 105 can be internal electrodes positioned proximate to blockage 305 and coupled to device 100, which may include a defibrillator or pacing machine, by wires 120. Power supply 115 may include a battery or AC power source, such as a connection to main lines in an outlet. In one embodiment, the user initiates application of the electrical current by inputting instructions to device 100 via a user interface with electrodes 105 internally positioned proximate to blockage 305.

Figure 9:
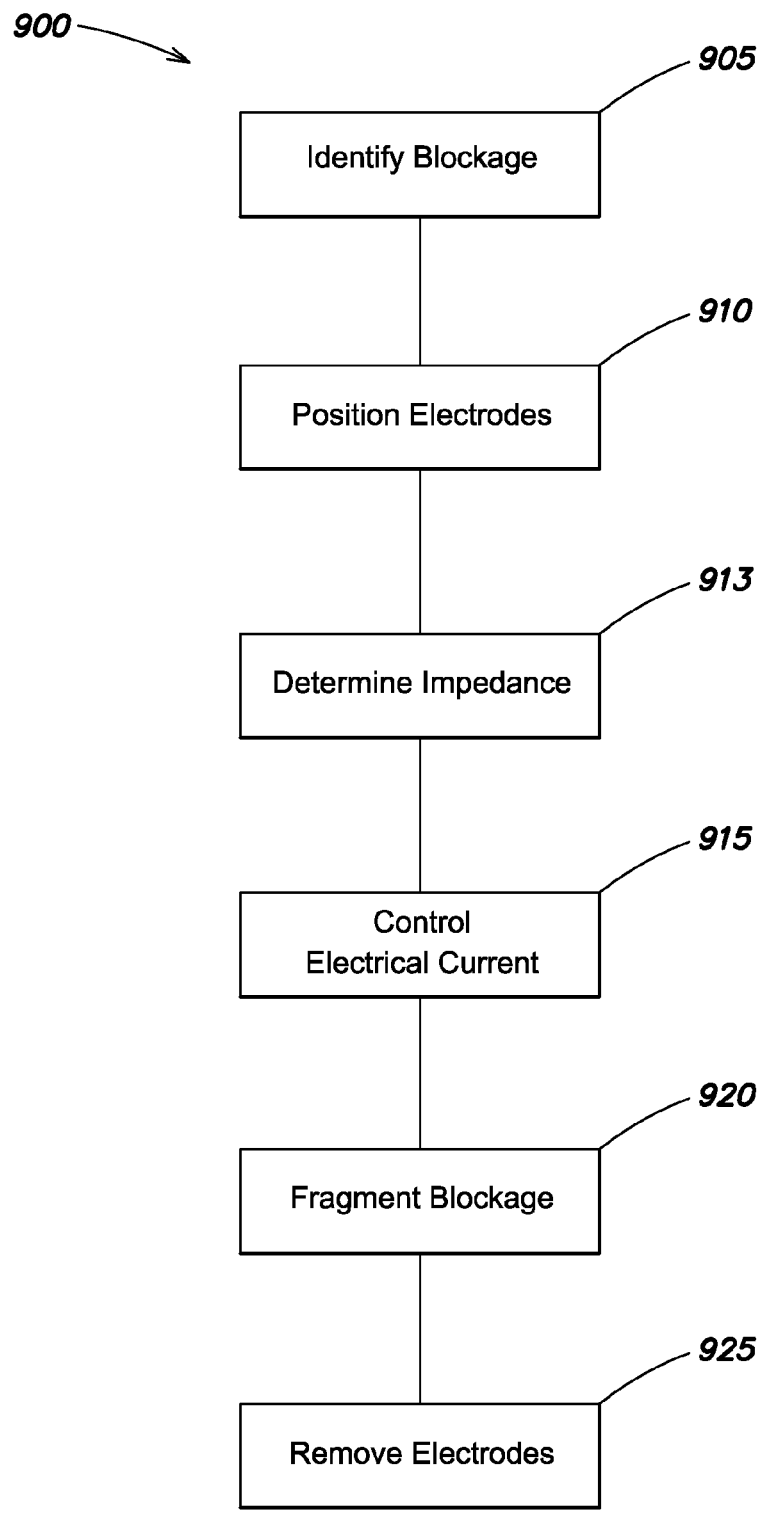
FIG. 9 is a flow chart depicting a method of ablating a blockage in a circulatory system of a subject in accordance with an embodiment.

FIG. 9 is a flow chart depicting a method 900 of ablating a blockage in a circulatory system of a subject. In one embodiment, method 900 includes an act of identifying a blockage (ACT 905). For example, a doctor can examine a subject to identify an at least partial blockage of a blood vessel. The blockage may include a thrombus or atherosclerotic condition in which plaque, calcium, or fatty deposits collect at a generally fixed location with respect to the inner surface of the blood vessel. These deposits can thicken and harden to at least partially block blood circulation within the blood vessel.

In one embodiment, method 900 includes an act of positioning electrodes (ACT 910). For example, at least one electrode can be positioned proximate to the subject. In one embodiment, positioning the electrodes (ACT 910) includes positioning a first electrode and a second electrode. For example, at least two electrodes may be positioned externally on a subject proximate to the location of the identified (ACT 905) blockage, or internally in the subject, proximate to a portion of the outer surface of the blood vessel where the blockage is located. In one embodiment, positioning the electrodes (ACT 910) includes positioning a first electrode external to the subject proximate to area of the blockage, and positioning a second electrode internal to the patient, proximate to an external surface of the blood vessel where the blockage is located. Positioning at least one electrode (ACT 910) can include locating electrodes proximate to any external surface of the subject's body, or any internal area of the subject's body so that current may be applied between at least two electrodes and through a blockage in one of the patient's blood vessels. In one embodiment, positioning the electrodes (ACT 910) includes the use of at least one fiber optic device to guide the electrodes to a desired position internal to the subject. The fiber optic device can include a remote camera.

Method 900 may also include an act of determining impedance of the blockage (ACT 913). In one embodiment, the electrodes 105 are used to measure blockage impedance, although it should be appreciated that a separate sensor may alternatively be used to detect blockage impedance. Determining impedance (ACT 913) may also include determining an estimated impedance, for example based on the size of the subject, or on a medical diagnosis that identifies the blockage. In one embodiment, method 900 includes an act of controlling electrical current (ACT 915). For example, a user may interface with an electrical stimulation device to provide current to positioned (ACT 910) electrodes. Controlling electrical current (ACT 915) can include providing current that follows a path between at least two electrodes and at least one blockage in a blood vessel of a subject. This current may have, for example, a value of between 20-80 mA. The user can interface with a controller or power supply to control current (ACT 915) that is applied to the subject in pulsed, continuous, or periodic cycles.

In one embodiment, controlling the current (ACT 915) includes adjusting the current responsive to the determined impedance. For example, a high impedance, approaching 200 ohms, can cause the electrical current to be adjusted downwards, and a low impedance, approaching 25 ohms, can cause a upward adjustment in current. Current can be controlled based on impedance levels that are determined before, during, between, or after electrical current treatment is applied to the subject. In one embodiment, partial deposit ablation is detected, for example by detecting an impedance reduction, and the current is decreased for the next application to the subject due to the reduced impedance of the deposit.

In one embodiment, method 900 includes an act of fragmenting the blockage (ACT 920). For example, application of controlled (ACT 915) current between positioned (ACT 910) electrodes can ablate or dissolve blood vessel blockages due to the kinetic energy or electron beam motion of the applied current. Alternatively, the flow of electrical current can induce an ionic flow of current in the vessel that acts (e.g., tugs or twists) on the molecular structure of the blockage. When current is applied, the blockage can begin to break apart at naturally occurring weak points such as cracks in the surface of the blockage. This breaks the blockage into particles that can dislodge from the inner surface of the blood vessel, improving blood flow at the area of the blockage. Fragmenting the blockage (ACT 920) may include ablating, dissolving, or breaking up the blockage into sufficiently small particles that can travel freely through the circulatory system. For example, fragmenting the blockage (ACT 920) may reduce the size of individual particles of the blockage to less than the diameter of a red blood cell, or less than the internal diameter of the subject's capillaries. In one embodiment, fragmenting the blockage (ACT 920) includes dissolving at least part of a thrombus attached to an inner surface of a blood vessel.

In one embodiment, method 900 includes an act of removing at least one electrode (ACT 925). For example, subsequent to application of controlled electrical current, external electrodes can be removed from the subject's body by the subject or by a user of the electrical stimulation device that applied the current. Any conductive gel or other material that facilitated conduction between the subject's body and the electrodes can be removed from the subject and cleaned from the surfaces of the electrodes. In one embodiment, subsequent to application of controlled electrical current, internally placed electrodes are removed (ACT 925) by a doctor, surgeon, or other user and the incision that allowed their internal entry into the subject is properly closed.

Figure 10:
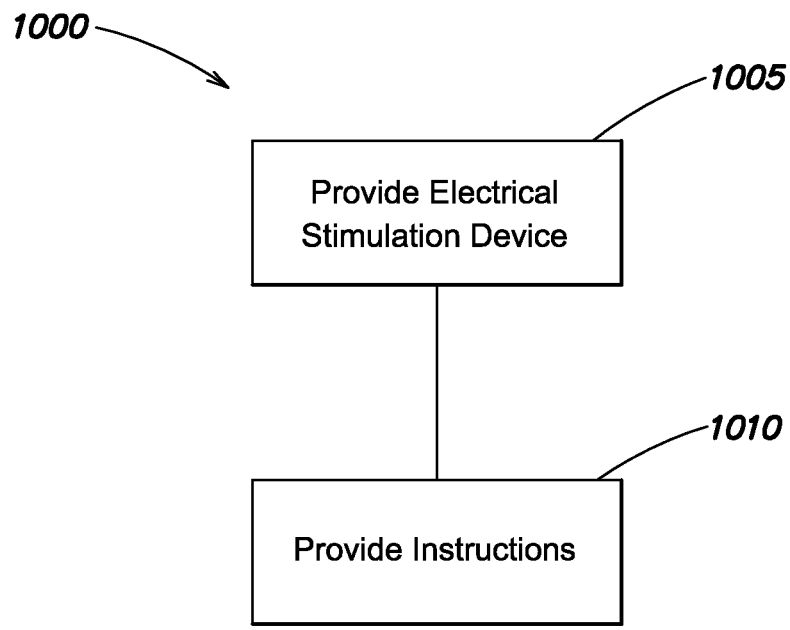
FIG. 10 is a flow chart depicting a method of facilitating vascular care of a subject in accordance with an embodiment.

FIG. 10 is a flow chart depicting a method 1000 of facilitating vascular care of a subject by, for example, ablating a blockage in the subject's circulatory system. In one embodiment, method 1000 includes the act of providing an electrical stimulation device (ACT 1005). In one embodiment, providing the electrical stimulation device (ACT 1005) includes providing a device having at least a first electrode and a second electrode. Providing the device (ACT 1005) can also include providing at least one controller and at least one power source. Providing the device (ACT 1005) can also include providing a device configured to apply electrical current that follows a path between a first electrode, a portion of a blood vessel that includes a blockage, and a second electrode.

In one embodiment, method 1000 includes an act of providing instructions to operate the electrical stimulation device (ACT 1010). The instructions can be provided (ACT 1010) via a user interface that is part of the device, or separately, such as by written instructions. The instructions can be provided audibly, visually, or combinations thereof. In one embodiment, providing instructions (ACT 1010) directs the user to identify a location of the portion of the blood vessel that includes the blockage. The provided (ACT 1010) instructions can also direct the user to position a first electrode and a second electrode proximate to the location of the portion of the blood vessel that includes the blockage, and to control an electrical current to follow a path between the first electrode and the second electrode that includes the blockage. In one embodiment, providing instructions (ACT 1010) directs the user to position the first electrode internal to the subject, external to the blood vessel that includes the blockage, and proximate to a first portion of an outer surface of the blood vessel, and to position the second electrode internal to the subject, external to the blood vessel that includes the blockage, and proximate to a second portion of the outer surface of the blood vessel. Providing instructions (ACT 1010) can also instruct the user to apply the electrical current to the blockage.

In some embodiments, providing instructions (ACT 1010) directs the user to position the first electrode external to the subject, proximate to the blockage, to position the second electrode external to the subject, proximate to the blockage, and to apply the electrical current to the blockage. The provided (ACT 1010) instructions can also direct the user to apply the electrical current to the blockage, and to remove the first electrode and the second electrode from the subject subsequent to application of the electrical current.

Experimental Results

In accordance with aspects of the present invention, clinical testing of an electrical stimulation device similar to that described above with respect to FIGS. 1-4 was performed on a study population of 12 male Yorkshire swine. The electrical stimulation device used during this testing included a pair of electrodes configured for external placement on the skin of the subject. The procedures described and performed during this testing were conducted in accordance with the Guide for the Care and Use of Laboratory Animals, USDA APHIS, Animal Welfare Act and/or in accordance with the Standard Operating Procedures of the test facility, which is an AAALAC accredited facility. Methods of euthanasia used during this testing were performed in accordance with accepted American Veterinary Medical Association (AVMA) guidelines.

The 12 swine were divided into 4 groups, with three animals in each group. There were three test groups (Groups 1, 2, and 3) and one control group (Group 4). After an acclimation period of approximately five days, all animals were examined and deemed healthy by a trained veterinarian, after which the study commenced. All animals had a thrombus (approximately two inches in length) created in the left femoral vein. Three days after thrombus creation an angiogram was performed, the thrombus occlusion severity was scored, and the thrombus of the test groups was treated with the trans-dermal electrical stimulation device and the thrombus occlusion severity reevaluated. The animals for Groups 1, 2, and 4 were survived for an additional 14 days post-treatment and the animals of Group 3 were survived for an additional 4 days post-treatment at which time the thrombus occlusion severity was rated and the animals euthanized. At necropsy a gross evaluation of the treated site, the heart and lungs was performed and the treated vessel collected with the heart and a lung sample.

Electrical treatment of the thrombus was successful in all treated animals. The average post treatment blood flow improvement was over 50%. Also of note was the return of blood flow with left femoral vein thrombi that were close to or at 100% occlusion. A first set of electrical parameters produced thrombolysis in one of the animals, and for repeatability, the same electrical parameters were used for 5 more animals. In all animals of Groups 1 and 2 (6 total) all treated thrombi were reduced with improved blood flow. Electrodes with 10% chloride gel produced noticeable dermal reactions, while the use of ¾% chloride gel electrodes did not result in any dermal changes during treatment. Using 50% lower total treatment energy on one animal compared to the total energy used for the successful results on 6 previous animals also produced the same thrombolytic effects. A 75 minute treatment was found to be effective, and increasing the treatment time from 75 to 105 minutes had no measureable effect. For two animals, a 30 minute treatment produced the same results as a treatment time of 75 minutes.

Overview of Test Methodology

The study population consisted of 12 Yorkshire swine. The animals were subjected to thrombus formation in the left femoral vein on Day 0 and allowed to recover. On Day 3 post-thrombus formation, the animals underwent left femoral vein angiography to confirm thrombus formation, after which the animals of Groups 1-3 (i.e., all but the control Group 4) were treated with a thrombolytic electrical stimulation device similar to that described above with respect to FIGS. 1-4. The animals were allowed to recover and were observed until euthanasia. Euthanasia and necropsy was performed on Day 7 (three animals total, from Group 3) and Day 17 (nine animals total, three from each of Groups 1, 2 and 4).

The animals of Groups 1 and 2 were treated the same, except one animal of Group 1 (animal number 550) was treated for 105 minutes. The animals of Group 3 were all treated slightly different relative to the animals of Groups 1 and 2 to determine when dermal changes occur by changing 10% chloride gel pads every 15 min, to determine the time to thrombolysis by taking angiograms every 15 minutes, to determine the dermal reaction effect of using ¾% chloride gel electrodes, and to determine the effect of using approximately 50% less total treatment energy. Table 1 below illustrates the overall test methodology.

TABLE 1

| Group | Group ID | Number of Animals | Weight/ Sex | Thrombus Creation Procedure | Treatment (Day 3 post Thrombus Creation) | Imaging | Survival Period |
| --- | --- | --- | --- | --- | --- | --- | --- |
| 1 | Test A | 3 | 40 ± 5 Kg/M | Create thrombus in left femoral vein (Day 0) | 175 ms pulse width, 170 pulses per minute, 15 ma for 75 minutes | Angiograms: pre-thrombus creation Angiogram: pre-treatment | 14 ± 2 Days post-treatment (17 ± 2 Days post-thrombus induction) |
| 2 | Test B | 3 | | | | | |

TABLE 1-continued

| Group | Group ID | Number of Animals | Weight/ Sex | Thrombus Creation Procedure | Treatment (Day 3 post Thrombus Creation) | Imaging | Survival Period |
|---|---|---|---|---|---|---|---|
| 3 | Test C | 3 | | | Vena cava filter implanted before treatment, See Table 2 below for treatment | Angiogram: post-treatment Digital photograph of explanted vein | 4 ± 1 Day post-treatment (7 ± 1 Days post-thrombus induction) |
| 4 | Control | 3 | | | No treatment for control group, angiogram only | | 14 ± 2 Days post-treatment (17 ± 2 Days post-thrombus induction) |

Table 2 below illustrates the test methodology used with the animals of Group 3.

TABLE 2

| Group 3 (Treatment Order/ Animal Number) | Treatment |
|---|---|
| 1/549 | 10% chloride gel electrodes, 175 ms pulse width, 170 pulses per minute, 15 ma current, total treatment time 75 minutes, electrodes changed and angiogram performed every 15 minutes |
| 2/556 | ¾% chloride gel electrodes, 175 ms pulse width, 170 pulses per minute, 15 ma current, total treatment time 75 minutes, electrodes changed and angiogram performed at 15 and 30 minutes |
| 3/552 | ¾% chloride gel electrodes, 80 ms pulse width, 170 pulses per minute, 15 ma current, total treatment time 75 minutes, electrodes changed and angiogram performed at 15 and 30 minutes |

Details of Test Methodology and Materials

Twelve male, Yorkshire pigs were enrolled in the study weighing approximately 40 kg±5 kg upon arrival at the test facility. All animals were maintained under acclimation conditions for 5-6 days prior to examination and release by the facility veterinarian. During this period, the animals were handled daily so they became acclimated to close human contact, and all animals were deemed healthy by the facility veterinarian at the end of the acclimation period. Each animal was uniquely identified by an ear tag on either the right or left ear, and a tattoo was applied to the opposite ear with the tag number. In addition, identification cards were affixed to each pen and displayed the animal number, gender, study director, and study number.

The animals were housed in rooms of the testing facility where the temperature and the humidity was monitored daily. The environmental conditions for swine are typically a room temperature between 61-81° F. and a relative humidity between 30-70%. The temperature was within range during the entire study and the average relative humidity was within range during the entire study except once in one of the rooms (which was out of range at 77% relative humidity on the fifth day of acclimation). During this deviation, the Study Director was notified and determined that there were no notable deviations which had an impact on the study outcome. The animals had 12 hours of light followed by a 12 hour dark cycle, and tap water was provided to the animals by an automatic watering system. The system was checked daily to assure it was operating appropriately. The animals were fed LabDiet® Laboratory Porcine Grower Diet 5084 and fed twice daily. Post-surgical inappetence was addressed through feeding treats or feed enrichment (fruit, vegetables, NutriCal and other similar treats) to promote eating. A variety of treats were introduced prior to the surgical procedure. All animals were fasted at least 8 hours prior to surgery, and body weights were obtained using a calibrated scale.

Each animal was sedated and then anesthetized according to test facility procedure prior to surgery preparation. Each animal was sedated with a mixture of Ketamine (20 mg/kg), Xylazine (2 mg/kg) and Atropine (0.04 mg/kg) administered intramuscularly (IM). Each animal was intubated and then received inhalant isoflurane at 2.5%-4% for induction and 0.5-4% for maintenance of anesthesia, delivered through a volume-regulated vaporizer. An intravenous catheter of appropriate size was placed in the marginal ear vein. Lactated Ringer's solution was administered at 10 ml/kg/hr for the duration of the surgical procedures.

For each animal the hair was clipped from the inguinal area. The animal was positioned in dorsal recumbency. The operative areas were then cleaned with three alternating scrubs of povidone-iodine surgical solution and 70% alcohol. Once the alternating scrubs were complete, a final application of povidone-iodine surgical solution was applied and allowed to dry. The areas were draped for aseptic surgery.

For all animals in the study, the left femoral vein was accessed with an 8F introducer and a baseline angiogram of the vasculature was performed under fluoroscopy. A 6 mm balloon was placed in the femoral vein and a push-pull method was used to denude the intimal layer of the vessel. The balloon was positioned distal to the injury and inflated to occlude the vein. Thrombin (1000 units) was injected through the introducer. The balloon remained inflated for 30 minutes to allow thrombus formation, after which the balloon was deflated and removed. An angiogram was performed to confirm thrombus creation. The thrombus was approximately two inches in length. The introducer sheath was removed and the vessel held until bleeding stopped. The animals were allowed to recover from anesthesia and returned to individual pens for twice daily observations.

For all of the animals in the test groups (i.e., Groups 1, 2, and 3), during treatment with the thrombolytic electrical stimulation device, two externally placed electrodes were used, with the top (anterior) electrode (or pad) being connected to the positive terminal of the electrical stimulation device, and the bottom (posterior) electrode (or pad) being connected to the negative (ground) terminal of the electrical stimulation device. The electrical stimulation device had a maximum voltage output of 45 volts. The electrodes used during the test study were Pedia MFE (Pediatric Multifunction Electrodes) electrodes available from Bio-Detek, Inc. of Pawtucket R.I., a subsidiary of ZOLL Medical Corporation of Chelmsford, Mass. These electrodes are solid electrodes that are round in shape, have a diameter of approximately 6 cm, an electrode area of approximately 30 cm$^2$ and were stored, prior to use, at room temperature (approximately 20-25° C.). During treatment, an electrically conductive hydrogel was used, which contained 10% Chloride (Groups 1 and 2 and one animal in Group 3) or ¾% Chloride (two animals in Group 3). Standard laboratory precautions and aseptic handling techniques were observed during treatment.

Groups 1, 2 and 4 Treatment

Three days after thrombus creation, an angiogram was performed and the thrombus occlusion severity was scored as: 1-(0-25% occlusion), 2-(26-50% occlusion), 3-(51-75% occlusion), and 4-(76-100% occlusion). For the animals of Groups 1 and 2, electrodes with a 10% chloride gel were placed on the animal and electrical current was applied using pulses of current having an amplitude of 15 mA and a pulse width of 175 ms at a frequency of 170 pulses per minute for a duration of 75 minutes (See Table 1). Given that the impedance between the pair of electrodes was approximately 500 Ohms, the applied voltage was approximately 7.5 volts. After treatment an angiogram was performed and the thrombus occlusion severity scored by angiogram. The animal was then allowed to recover. The treatment for one animal, Number 550, consisted of an additional 30 minutes.

Group 3 Treatment

All animals of Group 3 were implanted with a vena cava filter prior to treatment (a typical clinical deep vein thrombosis procedure) to determine if any thrombi were dislodged and the size of any thrombi trapped by the filter. An angiogram of the filter was performed pre-treatment and post-treatment.

The first animal treated in Group 3 (animal Number 549) was treated using 10% chloride gel electrodes using pulses of current having an amplitude of 15 mA and a pulse width of 175 ms at a frequency of 170 pulses per minute for a duration of 75 minutes. The electrodes were changed every 15 minutes, the pad to skin area condition was noted and photographed, and the thrombus occlusion severity scored by angiogram.

The second animal treated in Group 3 (animal number 556) was treated using ¾% chloride gel electrodes, but again using pulses of current having an amplitude of 15 mA and a pulse width of 175 ms at a frequency of 170 pulses per minute for a duration of 75 minutes. The electrodes were changed once after 15 minutes, the skin condition was noted and photographed, and the thrombus occlusion severity scored by angiogram.

The third animal treated in Group 3 (animal Number 552) was also treated using ¾% chloride gel electrodes. However, on this animal, pulses of current having an amplitude of 15 mA but a pulse width of 80 ms were applied at a frequency of 170 pulses per minute for a duration of 75 minutes. Thus, the total amount of energy applied to this third animal was approximately 50% less than that of the first and second animals. The electrodes were changed at 15 and 30 minutes, the skin condition was noted and photographed, and the thrombus occlusion severity scored by angiogram.

Table 3 below summarizes the treatment performed on the various groups.

TABLE 3

Treatment: Electrodes, Electrical Parameters, Angiogram Times

| Animal Number | Group ID | Electrode Type | Electrode Gel Chloride Concentration % | Current (ma) | Pulse Width (ms) | Pulses per min | Total treatment Time min | Angiogram Times During Treatment min |
|---|---|---|---|---|---|---|---|---|
| 544 | 1 | Pedi MFE | 10 | 15 | 175 | 170 | 75 | 0, 75 |
| 546 | 1 | Pedi MFE | 10 | 15 | 175 | 170 | 75 | 0, 75 |
| 550 | 1 | Pedi MFE | 10 | 15 | 175 | 170 | 105 | 0, 75, 105 |
| 547 | 2 | Pedi MFE | 10 | 15 | 175 | 170 | 75 | 0, 75 |
| 551 | 2 | Pedi MFE | 10 | 15 | 175 | 170 | 75 | 0, 75 |
| 554 | 2 | Pedi MFE | 10 | 15 | 175 | 170 | 75 | 0, 75 |
| 549 | 3 | Pedi MFE | 10 | 15 | 175 | 170 | 75 | 0, 15, 30, 45, 60, 75 |
| 552 | 3 | Pedi MFE | ¾ | 15 | 80 | 170 | 75 | 0, 15, 30, 75 |
| 556 | 3 | Pedi MFE | ¾ | 15 | 175 | 170 | 75 | 0, 15, 30, 75 |
| 548 | 4 | Pedi MFE | 10 | 15 | 175 | 170 | 75 | Na |
| 553 | 4 | Pedi MFE | 10 | 15 | 175 | 170 | 75 | Na |
| 555 | 4 | Pedi MFE | 10 | 15 | 175 | 170 | 75 | Na |

Na—not applicable

Recovery

For each animal, after completion of the surgical procedure, inhalant anesthetic gases were discontinued and the animal was allowed to recover Animal monitoring continued until extubation when the animal was transferred to the home pen for twice daily, a.m. and p.m., pen-side health assessment checks including mortality/moribundity. Observations were recorded per the test facility's standard operating procedures. When the animals were fully awake they were allowed free access to food and water. Buprenorphine was given at 0.01 mg/kg pre-operatively, but no additional pain management was required Animals in the test Groups 1, 2 and 3 received 200 mg aspirin and 75 mg clopidogrel (Plavix®) once daily post-treatment until euthanasia. The animals of Group 4 (Control) did not receive aspirin or Plavix treatment.

A twice daily cage side animal health assessment was performed for all animals during the survival period according to test facility guidelines. General health assessments were conducted by trained testing facility technician(s) twice per day, approximately 8 hours apart from the time of animal receipt through the end of the animal's stay at the facility. At each check, a technician walked through the study room to confirm that all animals had eaten, to look for the presence of urine and fecal matter in each cage and to look for abnormal physical signs such as lethargy, emaciation, abnormal vocalization, missing anatomy, laceration, and abnormal behavior. Animals were not removed from their cages or pens during these daily assessments. All findings were generally normal and documented. In addition, clinical observations were conducted twice daily post-implantation until euthanasia. The clinical observations consisted of observing the skin area where the electrodes contacted the skin, a lameness check and checking for any other symptoms.

Pathology Procedures

Prior to euthanasia all animals had an angiogram performed to assess the treated vessel thrombus occlusion severity score, and the animals of Group 3 additionally had an angiogram of the vena cava filter to assess major thrombus collection. Following the angiogram, all animals were given an intravenous injection of sodium heparin (10,000 I.U.) to prevent any further thrombus formation, and sodium pentobarbital (150 mg/kg) was administered intravenously to cause euthanasia in accordance with accepted American Veterinary Medical Association (AVMA) guidelines. The animals of Group 3 were euthanized at four days post treatment, and the animals of Groups 1, 2, and 4 were euthanized at fourteen days post treatment.

All euthanized animals were subject to necropsy where the specific focus was on the left femoral vein, heart and lungs. The left femoral vein was exposed and photographed and then removed, examined grossly, and photographed again. In some instances the vessel was cut open in order to view the inner lumen and photographed. The heart and lungs were examined grossly. The heart and a lung sample were removed. All samples were stored in 10% (NBF) neutral buffered formalin. The animals of Group 3 also had the vena cava filter removed and examined.

Results

Twelve Yorkshire swine successfully underwent thrombus formation in their left femoral vein and recovered as expected in accordance to the study protocol. All animals gained weight from surgery to euthanasia. The average weight increase from surgery weight to euthanasia weight for all animals was 1% per day, or a 4 day average weight gain of 2.3 kg for the animals of Group 3, and a 14 day average weight gain of 17.1 kg for the animals of Groups 1, 2 and 4.

Groups (1, 2 and 4)

The treatment for Groups 1 and 2 was the same, allowing the data for Groups 1 and 2 to be combined. All six animals (Groups 1 and 2 combined) responded to treatment. The mean thrombus occlusion severity score before treatment for the combined Groups (1 and 2) was 3.3, and after treatment, the mean thrombus occlusion severity score was 1.2, a reduction by 2.1 or 26% to 50%. The treatment time for all six animals of the combined Groups 1 and 2 was 75 minutes, except for one animal Number 550 that received an additional 30 minutes treatment. The thrombus occlusion severity score for animal number 550 was 2 after 75 minutes, and after an additional 30 minutes the thrombus occlusion severity score remained at 2.

The average thrombus occlusion severity score for Group 4 (Control) on Day 3 was 3.0.

At euthanasia the effects of vessel wall thickening, a result of the model, confounded the angiogram thrombus occlusion severity scoring. As a result the day 14 pre-euthanasia thrombus occlusion severity scores are not directly the result of residual thrombus, but are influenced by the presence of vessel wall thickening. No meaningful comparisons to the day 14 thrombus severity scores can be made because of the presence of vessel wall thickening.

Group 3

The severity scores for the three animals of Group 3 on Day 3 were 2, 3 and 4. Table 4 below summarizes the thrombus occlusion severity score data for the 4 different groups of animals.

TABLE 4

Thrombus Occlusion Severity Score Data

| Animal Number | Group | Severity Score Before Treatment | Severity Score After 75 min Treatment | Severity Score Pre-Euthanasia* | Days Treatment to Euthanasia |
|---|---|---|---|---|---|
| 544 | 1 | 3 | 1 | 1 | 14 |
| 546 | 1 | 3 | 1 | 1 | 14 |
| 550 | 1 | 4 | 2* | 4 | 14 |
| 547 | 2 | 3 | 1 | 2 | 14 |
| 551 | 2 | 4 | 1 | 2 | 14 |
| 554 | 2 | 3 | 1 | 1 | 14 |
| 549 | 3 | 4 | 2 | 3 | 4 |
| 552 | 3 | 3 | 1 | 1 | 4 |
| 556 | 3 | 3 | 1 | 2 | 4 |
| 548 | 4 | 2 | na | 1 | 14 |
| 553 | 4 | 3 | na | 2 | 15 |
| 555 | 4 | 4 | na | 3 | 14 | na—not applicable
*Treated for 105 minutes

The animals of Group 3 were treated differently than the animals of Groups 1 and 2 to reduce or eliminate any dermal reaction, to determine the effects of a vena cava filter, to reduce the effects of vessel wall thickening by reducing the time from treatment to euthanasia from 14 days to 4 days, and to determine the effects of reducing the total electrical treatment energy by 50%.

All animals of Group 3 were implanted with a vena cava filter prior to treatment on Day 3. The first animal (animal number 549) was treated with the same electrode type and electrical settings as the animals of Groups (1 and 2), but the 10% chloride electrodes were changed every 15 minutes. Every 15 minutes, an angiogram of the treated vessel was performed for thrombus occlusion severity scoring and the skin-to-pad area was observed for any signs of dermal reaction. Angiography of the vena cava filter was performed post-treatment to look for any evidence of large thrombus capture. The thrombus occlusion severity score dropped by 1 after 15 minutes, and the skin-to-pad area was observed as focal "burning" in appearance; however, the skin reaction was superficial. After 60 minutes the thrombus occlusion severity score dropped another point to 2. After 75 minutes of treatment, the thrombus occlusion severity score was 2, the vena cava filter was observed to be clear under fluoroscopy, the top skin-to-pad area was "burned" in appearance, and the bottom skin-to-pad area was clear.

To reduce or eliminate the dermal reaction, the second animal (animal number 556) was treated with the same electrical settings as the first animal of Group 3, but using electrodes with ¾% chloride gel. At 15 and 30 minutes, an angiogram of the treated vessel was performed, the thrombus occlusion severity was scored, and the skin-to-pad area was observed for any signs of dermal reaction. The electrode pads were not changed during treatment, but at 15 and 30 minutes the pads were lifted, photographs were taken of the skin-to-pad areas, and the electrodes re-applied. The thrombus occlusion severity score remained the same at 3 after 15 minutes and there was no dermal reaction evident on the skin-to-pad area of either electrode. After 30 minutes the thrombus occlusion severity score dropped by 2 to a score of 1 and no dermal reaction was detected. After 75 minutes of treatment the thrombus occlusion severity score remained at 1 with no evidence of dermal reaction.

The third animal (animal number 552) repeated the use of ¾% Chloride gel electrodes with the same electrical settings as the first Group 3 animal. However, the total energy delivered during treatment was reduced by approximately 50% by reducing the pulse width to 80 ms. At 15 and 30 minutes an angiogram was performed of the treated vessel, the thrombus occlusion severity was scored, and skin-to-pad area was observed for any signs of dermal reaction. The electrode pads were not changed during treatment, but at 15 and 30 minutes the pads were lifted, photographs were taken of the skin-to-pad areas, and the electrodes re-applied. The thrombus occlusion severity score went down one point to 2 after 15 minutes and the dermal reaction was undetectable. After 30 minutes the thrombus occlusion severity score went down one point again to 1 and the dermal reaction remained clear and unchanged. After 75 minutes of treatment the thrombus occlusion severity score was 1, the dermal reaction was clear, and the vena cava filter was observed to be clear under fluoroscopy.

Necropsy Results

Tissue collection for all animals consisted of the treated portion of the left femoral vein, the heart, and a lung sample. The vena cava filter was also explanted for two of the Group 3 animals (animal numbers 549 and 556). The vena cava filter of the third Group 3 animal (animal number 552) was placed in the proximal right iliac and was not retrieved.

The injured area of the left femoral vessel wall was thickened in many of the animals and was found to interfere with the thrombus occlusion severity score determined by angiogram at the Day 14 time point. This was the motivation to reduce the time from treatment to euthanasia from 14 days used for Groups 1 and 2 to 4 days for Group 3. Necropsy results are shown in Table 5 below.

Photographs of the treated skin-to-pad area showed evidence of "burning" which cleared after a few days post treatment, and by day 14 was essentially healed in 9 animals. This description of the epidermal change as "burning" is based upon the way it looked visually; however after 14 days there was no scar or any other evidence of epidermal trauma. For this reason the "burning" description of the epidermal reaction was found to be a superficial effect.

Photographs of the treated vessel exposed, removed and dissected shows the vessel wall thickening present 14 days after treatment and the lack of vessel wall thickening 4 days after treatment.

The clinical investigation described above was used to determine treatment parameters, electrodes, and electrical parameters capable of achieving thrombolytic effects in a swine femoral vein thrombosis model. As known to those skilled in the art, the porcine model used in the clinical testing described herein is an established in vivo animal model having a strong correlation to human subjects. Accordingly, it is believed that the various electrical parameters and setting used in this investigation could be used on human subjects. For example, 15 mA pulses of current having a duration of 80-175 ms could be applied to the body of a human subject using transdermal electrodes having a ¾% chloride gel at a frequency of between 100 and 175 pulses per minute for a duration of 30 to 75 minutes to ablate a thrombus. Should the human subject be conscious during the procedure, a lesser amount of energy may be used with similarly constructed transdermal electrodes, such as by applying 2 mA-8 mA pulses of current having a duration of 2 ms at a frequency of between 50 and 100 pulses per minute at an applied voltage of between 5 and 10 volts to reduce discomfort of the subject during the procedure. Such therapy may be applied to the subject for a duration of between one and 8 hours.

TABLE 5

Necropsy Results

| | | Left Femoral Vein | | | | | |
|---|---|---|---|---|---|---|---|
| Animal Number | Group | Thrombus | Vessel Wall Thickening | Heart | Lungs | Vena Cava Filter | Days Treatment to Euthanasia |
| 544 | 1 | Na | y* | normal | bulk on left caudal lung | not used | 14 |
| 546 | 1 | Na | n* | normal | normal | not used | 14 |
| 550 | 1 | Na | y* | normal | normal | not used | 14 |
| 547 | 2 | Na | Yes | normal | normal | not used | 14 |
| 551 | 2 | No | Yes | normal | normal | not used | 14 |
| 554 | 2 | Na | n* | normal | normal | not used | 14 |
| 549 | 3 | Yes | No | tsivsg | normal | small segments soft clot | 4 |
| 552 | 3 | Yes | No | tsivsg | normal | placed at proximal right iliac | 4 |
| 556 | 3 | Yes | No | tsivsg | normal | clot present, approx 2 cm long | 4 |
| 548 | 4 | Na | n* | normal | normal | not used | 14 |
| 553 | 4 | Small | yes | normal | normal | not used | 15 |
| 555 | 4 | Na | y* | normal | normal | not used | 14 | na—not available
*based on photographs tsivsg-thin segment intra-ventricular septal groove As illustrated in Table 5, the gross necropsy results of the heart and lungs at 14 days post-treatment were generally normal, and after 4 days post treatment, the lungs were normal and the heart showed a thin segment along the intra-ventricular septal groove. In the two instances in which the vena cava filter was active after 4 days post treatment, the explanted filter collected small thrombi, one about 2 cm long and narrow.

Although the clinical testing described herein was performed using only electrical stimulation to ablate blockages, such as a thrombus in the femoral vein of swine, it should be appreciated that electrical stimulation may also be performed in combination with other therapies traditionally used to treat thrombi. For example, electrical stimulation such as described herein may be used in combination with the administration of a thrombolytic drug such as Tissue Plasminogen Activator (TPA) or recombinant TPA (rTPA), or with the administration of an anticoagulant drug such as heparin, or a low molecular weight heparin, such as Bemiparin, Certoparin, Dalteparin, Enoxaparin, Nardoparin, Parnoparin, Reviparin, or Tinzaparin.

As described herein, the electrical stimulation device may be used, alone or in combination with drug therapy to treat a wide variety of thrombi, such a deep vein thrombosis, pulmonary embolism, coronary clots, or other types of vascular blockages, such as plaque. During treatment, physiological parameters, such as temperature, impedance, pH, etc. may be monitored, and the electrical parameters of the electrical stimulation device adjusted accordingly. These adjustments may be performed manually (e.g., by a treating physician or technician adjusting the electrical parameters of the stimulation device) or automatically by the stimulation device based on a feedback control system. For example, where the impedance that is sensed between electrodes of the electrical stimulation device decreases during treatment, a higher value of current may be used, the duration of pulses may be increased, the frequency of the pulses may be increased, or combination thereof.

Having now described some illustrative embodiments of the invention, it should be apparent to those skilled in the art that the foregoing is illustrative and not limiting, having been presented by way of example. In particular, although many of the examples presented herein involve specific combinations of method acts or system elements, it is understood that those acts and those elements may be combined in other ways to accomplish the same objectives. Acts, elements and features discussed only in connection with one embodiment are not intended to be excluded from a similar role in other embodiments.

Note that in FIGS. 1 through 10, the enumerated items are shown as individual elements. In actual implementations of the systems and methods described herein, however, they may be inseparable components of other electronic devices such as a digital computer. Thus, actions described above may be implemented at least in part in software that may be embodied in an article of manufacture that includes a program storage medium. The program storage medium includes data signals embodied in one or more of a computer disk (magnetic, or optical (e.g., CD or DVD, or both)), non-volatile memory, tape, a system memory, and a computer hard drive or other memory device.

From the foregoing, it will be appreciated that the systems and methods of ablating a blockage in a circulatory system of a subject by applying electric current to the subject in a non-invasive, minimally invasive, (e.g., laparoscopic or minor surgery), or general surgical manner as described herein afford an effective way to reduce blood circulation impedances.

Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements to single or plural configurations.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment in any manner consistent with the aspects and embodiments disclosed herein.

References to "or" may be construed as inclusive so that any terms described using "or" may indicate any of a single, more than one, and all of the described terms. Intervening embodiments, acts, or elements are not essential unless recited as such. Any solution to a problem, or any element or act presented herein in the alternative, for example using the word "or," is neither ambiguous nor indirect simply because it may be presented in the alternative.

One skilled in the art will realize the systems and methods described herein may be embodied in other specific forms without departing from the characteristics thereof. For example, blockages in the subject's blood vessels include partial blockages, and the subject may or may not be experiencing distress due to the blockage condition. The deposit need not be in a blood vessel. For example, a circuit can be formed between at least two electrodes and a deposit that is outside a blood vessel, such as in a duct. The subject may also remain conscious during the application of current to the blockage. By positioning the electrodes external to the blood vessel, even when inside the patient, the electrodes are positioned in a non-invasive, minimally invasive (e.g., laparoscopic or minor surgical), or general surgical manner, without inserting medical instruments such as stents or electrodes inside the blood vessels. Depending on the location and severity of the blockage as well as individual subject tolerance, no medication may be necessary and the electrical stimulation device can be an alternative to drug induced treatment. In some embodiments, mild sedation or anesthesia could be appropriate. The electrical stimulation device can also be an alternative for an invasive vascular surgical procedure where a portion of the blood vessel including the blockage is removed. Further, a DC current can be applied to the blockage for a time period, such as a 10 mA direct current for 24 hours, or until impedance measurements indicate that the deposit is ablated.

The foregoing embodiments are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A method of ablating a blockage in a blood vessel of a subject, comprising:
    positioning a first electrode internal to the subject and proximate to a first portion of an outer surface of a blood vessel that includes the blockage;
    positioning a second electrode internal to the subject and proximate to a second portion of the outer surface of the blood vessel,
    wherein the first electrode and the second electrode are positioned external to the blood vessel and proximate to the blockage; and
    conducting pulses of an electrical current between the first electrode and the second electrode and along a path that includes the blockage, wherein the pulses are conducted at a frequency configured to ablate the blockage and facilitate blood flow in the blood vessel.

2. The method of claim 1, wherein conducting pulses of the electrical current includes conducting pulses of an electrical current having an amplitude between approximately 2 milliamperes and 8 milliamperes at a frequency between approximately 50 and 100 pulses per minute for a duration of approximately 1-8 hours.

3. The method of claim 1, wherein conducting pulses of the electrical current includes conducting pulses of an electrical current having an amplitude of approximately 15 milliamperes at a frequency between approximately 100 and 175 pulses per minute for a duration of approximately 30 to 75 minutes.

4. The method of claim 1, wherein at least some of the pulses have pulse widths of approximately 175 milliseconds.

\* \* \* \* \*